United States Patent
Kato

(10) Patent No.: US 9,816,883 B2
(45) Date of Patent: Nov. 14, 2017

(54) CURRENT SOURCE CIRCUIT AND DETECTION CIRCUIT

(71) Applicant: AISIN SEIKI KABUSHIKI KAISHA, Kariya-shi, Aichi-ken (JP)

(72) Inventor: Manabu Kato, Nisshin (JP)

(73) Assignee: AISIN SEIKI KABUSHIKI KAISHA, Kariya-shi, Aichi-ken (JP)

( * ) Notice: Subject to any disclaimer, the term of this patent is extended or adjusted under 35 U.S.C. 154(b) by 0 days.

(21) Appl. No.: 15/287,171

(22) Filed: Oct. 6, 2016

(65) Prior Publication Data

US 2017/0108386 A1    Apr. 20, 2017

(30) Foreign Application Priority Data

Oct. 19, 2015 (JP) ................ 2015-205500

(51) Int. Cl.

| | | |
|---|---|---|
| G01R 27/08 | (2006.01) | |
| G01L 1/22 | (2006.01) | |
| G01L 1/10 | (2006.01) | |
| G01N 17/00 | (2006.01) | |
| G01R 27/26 | (2006.01) | |
| G01R 27/00 | (2006.01) | |
| G01N 27/04 | (2006.01) | |
| G01N 27/02 | (2006.01) | |
| G01R 27/02 | (2006.01) | |
| G05F 3/26 | (2006.01) | |

(Continued)

(52) U.S. Cl.
CPC ............... *G01L 1/225* (2013.01); *G01L 1/10* (2013.01); *G01N 17/00* (2013.01); *G01N 27/02* (2013.01); *G01N 27/04* (2013.01); *G01R 27/00* (2013.01); *G01R 27/02* (2013.01); *G01R 27/2605* (2013.01); *G05F 3/26* (2013.01); *G01L 1/20* (2013.01); *G01L 1/22* (2013.01)

(58) Field of Classification Search
CPC ........ G01N 17/00; G01N 27/02; G01N 27/04; G01L 1/10; G01L 1/20; G01L 1/22; G01R 27/00; G01R 27/2605
USPC .......... 324/76.11–76.83, 439, 459, 549, 600, 324/606, 647, 649, 656, 665, 672, 679, 324/691, 705; 327/53, 132, 368, 490; 361/622
See application file for complete search history.

(56) References Cited

U.S. PATENT DOCUMENTS

| | | | | |
|---|---|---|---|---|
| 2005/0099233 A1* | 5/2005 | Zipper | ................ | H03F 3/45654 330/261 |
| 2014/0184184 A1* | 7/2014 | Yajima | ................ | G01R 19/165 323/274 |
| 2016/0305985 A1* | 10/2016 | Igarashi | ............. | G01R 19/0092 |

FOREIGN PATENT DOCUMENTS

| | | |
|---|---|---|
| JP | 54-098266 A | 8/1979 |
| JP | 05-236669 A | 9/1993 |
| JP | 2011-242312 A | 12/2011 |

* cited by examiner

*Primary Examiner* — Giovanni Astacio-Oquendo
*Assistant Examiner* — Raul Rios Russo
(74) *Attorney, Agent, or Firm* — Sughrue Mion, PLLC

(57) ABSTRACT

A current source circuit flowing an output current to at least one detection element including a first terminal to which a first voltage is supplied and a second terminal being connected to the current source circuit includes a reference resistance, a current mirror circuit including at least one first transistor and at least one second transistor, and a control circuit controlling a voltage of a common wire that is connected to a terminal provided at the first transistor and a terminal provided at the second transistor such that a voltage (Continued)

of a terminal provided at the reference resistance comes to be equal to a reference voltage.

14 Claims, 4 Drawing Sheets

(51) Int. Cl.
  *H02B 1/26* (2006.01)
  *G01L 1/20* (2006.01)

CURRENT SOURCE CIRCUIT AND DETECTION CIRCUIT

CROSS REFERENCE TO RELATED APPLICATIONS

This application is based on and claims priority under 35 U.S.C. §119 to Japanese Patent Application 2015-205500, filed on Oct. 19, 2015, the entire content of which is incorporated herein by reference.

TECHNICAL FIELD

This disclosure generally relates to a current source circuit and a detection circuit.

BACKGROUND DISCUSSION

A known detection circuit detecting a physical quantity of a detection target by a detection element, for example, a semiconductor strain gauge, is proposed (For example, refer to JPS61-28081A (hereinafter referred to as Patent reference 1) and JP2011-242312A (hereinafter referred to as Patent reference 2)). The detection circuit outputs detection signals that are in response to a terminal voltage of the detection element.

Meanwhile, the terminal voltage of the detection element is defined by a resistance value of the detection element and a current (a constant current) supplied to the detection element. The current supplied to the detection element may vary due to the change of the temperature level or the mixture of noises. Accordingly, the variance of the current due to the change of the temperature level or the mixture of noises is desired to be inhibited.

A need thus exists for a current source circuit and a detection circuit which is not susceptible to the drawback mentioned above.

SUMMARY

According to an aspect of this disclosure, a current source circuit flowing an output current to at least one detection element including a first terminal to which a first voltage is supplied and a second terminal being connected to the current source circuit includes a reference resistance including a first terminal being connected to a first wire to which the first voltage is supplied, a current mirror circuit including at least one first transistor including a first terminal and a first control terminal that are connected to a second terminal of the reference resistance, and at least one second transistor including a second control terminal that is connected to the first control terminal, the current mirror circuit in which the second transistor includes the first terminal that is connected to the second terminal provided at the detection element, and in which the first transistor includes a second terminal that is connected to a second terminal provided at the second transistor, and a control circuit controlling a voltage of a common wire that is connected to the second terminal provided at the first transistor and the second terminal provided at the second transistor such that a voltage of the second terminal provided at the reference resistance comes to be equal to a reference voltage.

According to another aspect of this disclosure, a detection circuit includes two detection elements corresponding to a first detection element and a second detection element, the two detection elements each including a first terminal to which a first voltage is supplied, the two detection elements each changing a resistance value in response to a physical quantity of a detection target, a current source circuit being connected to second terminals provided at the two detection elements, the current source circuit supplying an output current to each of the detection elements, and a differential amplifier including an input terminal being connected to the second terminals provided at the two detection elements, the differential amplifier outputting detection signals by differently amplifying an input voltage. The first detection element is disposed so as to change a resistance value of the first detection element in response to the physical quantity of the detection target. The second detection element is disposed such that a changing ratio of a resistance value of the second detection element in response to the physical quantity of the detection target is different from a changing ratio of a resistance value of the first detection element. The current source circuit includes a reference resistance including a first terminal being connected to a first wire to which a first voltage is supplied, a current mirror circuit including a first transistor including a first terminal and a first control terminal that are connected to a second terminal provided at the reference resistance, and two second transistors each including a second control terminal that is connected to the first control terminal, the current mirror circuit in which the two second transistors includes respective first terminals, each of the first terminals being connected to a second terminal provided at the detection element, and in which the first transistor includes the second terminal that is connected to each of the second terminals provided at the two second transistors, and a control circuit including a first input terminal that is connected to a second terminal provided at the reference resistance, the control circuit including a second input terminal to which the reference voltage is supplied, the control circuit controlling a voltage of a common wire that is connected to the second terminal provided at the first transistor and the respective second terminals provided at the two second transistors such that a voltage of the second terminal provided at the reference resistance comes to be equal to a reference voltage.

BRIEF DESCRIPTION OF THE DRAWINGS

The foregoing and additional features and characteristics of this disclosure will become more apparent from the following detailed description considered with the reference to the accompanying drawings, wherein.

DETAILED DESCRIPTION

Hereinafter, first, second, and third embodiments will be explained. A voltage of a terminal indicates an electric potential difference between a ground GND and the terminal unless otherwise particularly explained.

Figure 1:
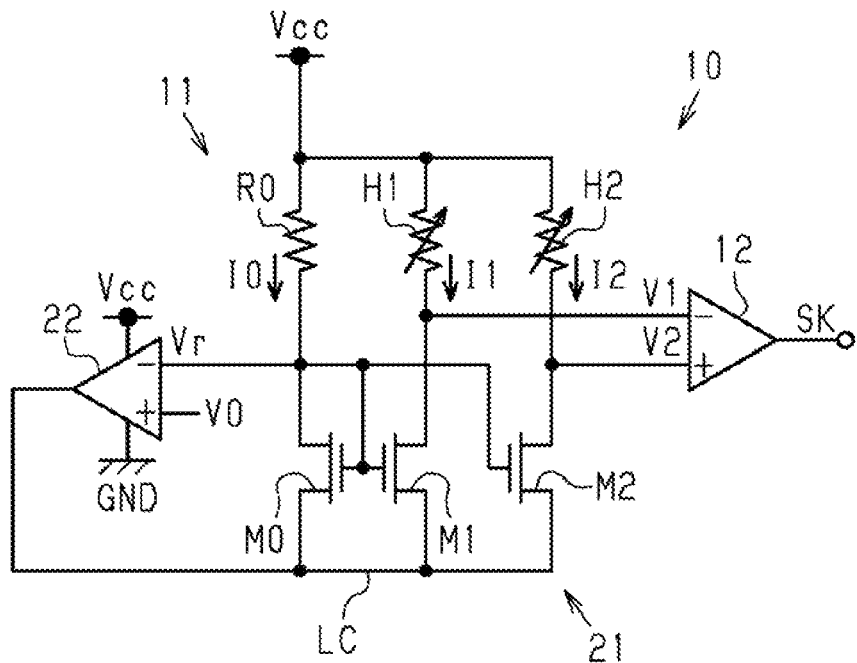
FIG. 1 is a schematic circuit diagram of a detection circuit according to a first embodiment disclosed here.

A first embodiment will hereunder be explained. As shown in FIG. 1, a detection circuit 10 outputs detection signals SK that are in response to plural (two in FIG. 1) detection elements H1, H2 (i.e., serving as a first detection element and a second detection element). Each of the detection elements H1, H2 changes a resistance value between terminals in accordance with a physical quantity of a detection target. Each of the detection elements H1, H2 corresponds to, for example, a strain gauge. The strain gauge corresponds to a semiconductor strain gauge that forms a resistance element, for example, a piezoresistance at a semiconductor substrate made of, for example, silicone. Each of the detection elements H1, H2 expands and contracts in response to the physical quantity, for example, a pressure level or an accelerated velocity that are applied to the detection elements H1, H2. For example, the detection element H1 is disposed to change the resistance value in response to the physical quantity. The detection element H2 is disposed to change the resistance value in response to the physical quantity in different proportions from the detection element H1. The detection circuit 10 outputs the detection signals SK that are in response to the change of the resistance value of each of the detection elements H1, H2.

The detection circuit 10 includes a current source circuit (a constant current circuit) 11 and a differential amplifier 12. The current source circuit 11 supplies output currents I1, I2 to the detection elements H1, H2, respectively. The differential amplifier 12 is connected to the detection elements H1, H2 and outputs the detection signals SK.

The current source circuit 11 includes a reference resistance R0, a current mirror circuit 21, and an operational amplifier 22 (i.e., serving as a control circuit). A first terminal of the reference resistance R0 is connected to a wire to which a high-potential power supply voltage Vcc (hereinafter, referred to as a power supply wire Vcc and serving as a first wire, a first voltage) is supplied. A second terminal of the reference resistance R0 is connected to the current mirror circuit 21. For example, similarly to the detection elements H1, H2, the reference resistance R0 corresponds to the resistance element that is provided at a semiconductor substrate. The temperature characteristics of the resistance values of the reference resistance R0 and of the detection elements H1, H2 are equal to one another. Thus, the temperature characteristics of the resistance values of the detection elements H1, H2 inhibit the voltage change at the second terminal of the reference resistance R0 when the gauge is not strained. The resistance value of the reference resistance R0 is set greater than the respective resistance values of the detection elements H1, H2.

The current mirror circuit 21 includes transistors M0, M1, M2 (i.e., serving as a first transistor and a second transistor). Each of the transistors M0, M1, M2 corresponds to, for example, a negative-channel metal oxide semiconductor transistor, or a n-channel MOS transistor. A drain terminal (a first terminal) of the transistor M0 is connected to the reference resistance R0. Drain terminals (first terminals) of the transistors M1, M2 are connected to second terminals provided at the detection elements H1, H2, respectively. The respective first terminals provided at the detection elements H1, H2 are connected to the power supply wire Vcc. Respective gate terminals (first and second control terminals) of the transistors M0, M1, M2 are connected to the drain terminal of the transistor M0. Respective source terminals (second terminals) of the transistors M0, M1, M2 are connected to a common wire LC. The transistors M0, M1, M2 are provided on, for example, a single semiconductor substrate and include the electrical characteristics that are equal to one another.

The drain terminal of the transistor M0 is connected to an inverted input terminal of the operational amplifier 22. A reference voltage V0 is supplied to a non-inverted input terminal of the operational amplifier 22. The output terminal of the operational amplifier 22 is connected to the common wire LC, that is, to the source terminals of the transistors M0, M1, M2. A high-potential power supply terminal of the operational amplifier 22 is connected to a power supply that includes a higher voltage than an input voltage, for example, to the power supply wire Vcc. A low-potential power supply terminal of the operational amplifier 22 is connected to a wire (hereinafter referred to as a power supply wire GND that serves as a second wire and a second voltage) to which a low-potential power supply voltage (for example, ground level corresponds to 0V) is supplied.

The inverted input terminal of the differential amplifier 12 is connected to the second terminal provided at the detection element H1. The non-inverted input terminal of the differential amplifier 12 is connected to the second terminal provided at the detection element H2. The differential amplifier 12 amplifies the potential difference between the respective second terminals of the detection elements H1, H2, and outputs the detection signals SK that include the amplified electric potential.

Figure 2A:
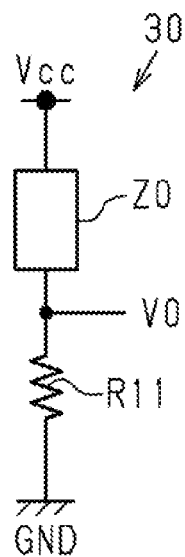
FIG. 2A is a schematic circuit diagram of a voltage generation circuit according to the first embodiment.

FIG. 2A illustrates an example of a voltage generation circuit generating the reference voltage V0. A voltage generation circuit 30 includes a load element Z0 and a resistance element R11. A first terminal of the load element Z0 is connected to the power supply wire Vcc. A second terminal of the load element Z0 is connected to a first terminal of the resistance element R11. A second terminal of the resistance element R11 is connected to the power supply wire GND. A second terminal of the load element Z0 works as an output terminal of the voltage generation circuit 30. That is, the voltage generation circuit 30 outputs the voltage of the second terminal of the load element Z0 as the reference voltage V0.

Figure 2B:
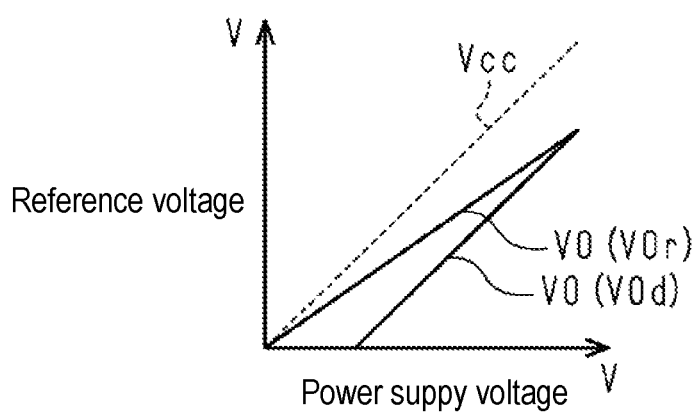
FIG. 2B is an output characteristic diagram of the voltage generation circuit according to the first embodiment.

For example, a Zener diode (a constant voltage diode) is used as the as the load element Z0. In this case, the voltage value of the reference voltage V0 corresponds to a value that is decreased from the power supply voltage Vcc by an amount of the voltage that is in accordance with the characteristic of the load element Z0. That is, as shown in FIG. 2B, the voltage difference occurred between the power supply voltage Vcc shown in a dotted-line and the reference voltage V0 shown in a solid line corresponds to a constant value irrespective of the change of the power supply voltage Vcc. A reference voltage generated by the load element Z0 corresponds to a reference voltage V0$d$.

For example, a resistance element is used as the load element Z0. In this case, the voltage value of the reference voltage V0 corresponds to a value that is between the power supply voltage Vcc and the power supply voltage GND, and that is calculated by the division of the power supply voltage Vcc and the power supply voltage GND by a ratio of the resistance value of the load element Z0 and the resistance value of the resistance element R11. In this case, as shown in FIG. 2B, the voltage value of the reference voltage V0 shown in the solid line corresponds to a value that is in proportion to the power supply voltage Vcc shown in the dotted line. The reference voltage generated by the load element Z0 corresponds to a reference voltage V0$r$.

As such, the voltage generation circuit 30 generates the reference voltage V0 in accordance with the load element Z0. The detection circuit 10, for example, as shown in FIG. 1, includes the voltage generation circuit 30.

Next, the operation of the detection circuit 10 will be explained.

The operational amplifier 22 controls the voltage of the common wire LC such that the voltage Vr of the non-inverted input terminal comes to be equal to the reference voltage V0. The reference resistance R0 flows the reference current I0 that is in response to the voltage Vr, that is, the voltage difference between the reference voltage V0 and the power source voltage Vcc, and in response to the resistance value of the reference resistance R0.

The current mirror circuit 21 flows the output currents I1, I2 to the transistors M1, M2, the output currents I1, I2 having the amounts that are equal to the amount of the reference current I0 flowing in the reference resistance R0. That is, the current source circuit 11 flows the output currents I1, I2 to the detection elements H1, H2, the output currents I1, I2 having the amount that are equal to the amount of the reference current I0. The respective currents flow in the transistors M0, M1, M2 flow to the power source wire GND from the common wire LC via elements of the operational amplifier 22.

The respective resistance values of the detection elements H1, H2 change in response to the physical quantity, for example, the applied pressure. For example, the resistance value of the detection element H1 increases in response to the applied physical quantity. For example, the resistance value of the detection element H2 decreases in response to the applied physical quantity. Accordingly, a voltage V1 (i.e., serving as an input voltage) of the second terminal provided at the detection element H1 decreases and a voltage V2 (i.e., serving as the input voltage) of the second terminal provided at the detection element H2 increases. The differential amplifier 12 outputs the detection signals SK in which the amount of difference between the voltages V1, V2 of the second terminals of the detection elements H1, H2, respectively, is amplified.

Here, for example, a constant current circuit disclosed in Patent reference 2 will be explained as a comparative example of the first embodiment. For convenience of comparison, the names of the components will be the same as the names of the components of the first embodiment.

The constant current circuit of the comparison example includes a transistor (a MOS transistor) being connected at a position between the current mirror circuit and the reference resistance. A source terminal of the transistor that forms the current mirror circuit is connected to a power supply wire GND. The operational amplifier controls a gate voltage of the transistor so as to make the terminal voltage of the reference resistance and the reference voltage be equal to each other. Accordingly, the constant current is obtained in response to the resistance value of the reference resistance and in response to the voltage between the terminals of the reference resistance.

In a case where signals supplied to the gate terminal are mixed with noises, the reference current I0 flowing in the reference resistance, that is, the output current supplied to the detection element, may greatly vary in proportion to a mutual conductance and noises of the transistor in order for the operational amplifier to control the gate voltage of the transistor. The reference current I0 flowing in the reference resistance, that is, the output current supplied to the detection element, may oscillate depending on the gain setting of the operation amplifier in order to control the gate voltage of the transistor based on the terminal voltage of the transistor.

On the other hand, according to the first embodiment, the operational amplifier 22 controls the voltage of the common wire LC being connected with the respective source terminals of the transistors M0, M1, M2. In a case where the noises are mixed to the output signals (the output voltages) of the operational amplifier 22, the respective voltages of the source terminals of the transistors M0, M1, M2 of the current mirror circuit 21 vary. In this case, comparing to the comparison example of Patent reference 2, that is, comparing to the comparison example in which the source terminal of the transistor forming the current mirror circuit is connected to the power source voltage GND, the voltage variation of the drain terminal of the transistor M0 may be less. The current flowing in the transistor M0 changes by the proportion of the voltage component of the noises and the resistance value of the reference resistance R0. The variance of the voltage applied between the gate terminal of the transistor M0 and the source terminal of the transistor M0 may be much less than the noises. As a result, the variance of the voltage applied between the respective gate terminals of the transistors M1, M2 and the respective source terminals of the transistors M1, M2 may be less. Each of the respective drain currents of the transistors M1, M2 changes by the proportion of the voltage component of the noises and the resistance value of the reference resistance R0. Accordingly, the variation of the output currents I1, I2 is inhibited.

The voltage generation circuit 30 shown in FIG. 2A generates the reference voltage V0 in response to the load element Z0. For example, in a case where the Zener diode is used as the load element Z0, the reference voltage V0 has a constant voltage difference relative to the power supply voltage Vcc. Accordingly, in the detection circuit 10 shown in FIG. 1, the value of the voltage difference occurred between the terminals of the reference resistance R0 is constant in response to the change of the power supply voltage Vcc. That is, the constant reference voltage I0 and the constant output currents I1, I2 may be gained in response to the change of the power supply voltage Vcc. Thus, the respective voltages V1, V2 of the second terminals of the detection elements H1, H2 may be inhibited from changing in response to the change of the power supply voltage Vcc. That is, the offset and the sensibility of the detection elements H1, H2 may be inhibited from changing in response to the change of the power supply voltage Vcc.

In a case where the resistance element is used as the load element Z0, the value of the reference voltage V0 is in proportion to the power supply voltage Vcc. Accordingly, in a case where the sensitivity of the detection elements H1, H2 that are in proportion to the power supply voltage Vcc may be gained, where the detection signals SK are inputted, and where the reference voltage of the processing circuit is in proportion to the power supply voltage Vcc, signals that have a few inaccuracies may be sent and received.

According to the first embodiment, following effects and advantages may be attained.

According to the current source circuit 11 of the first embodiment, the operational amplifier 22 controls the voltage of the common wire LC being connected with the respective source terminals of the transistors M0, M1, M2. When the temperature level changes, the operational amplifier 22 controls the voltage of the common wire LC in response to the characteristics of the gate voltage of the transistor M0 and the source current of the transistor M0 relative to the changed temperature level, or in response to the temperature characteristics of the reference resistance R0. Accordingly, the voltage Vr of the second terminal of the reference resistance R0 comes to be equal to the reference voltage V0. That is, the voltage applied between the terminals of the reference resistance R0 does not change in response to the change of the temperature level. Accordingly, the temperature characteristics of the transistor M0 of the output currents I1, I2 being supplied to the detection elements H1, H2 may be inhibited from varying.

In a case where the output signals (output voltage) of the operational amplifier 22 are mixed with noises, the voltage of the drain terminal of the transistor M0 may be inhibited from varying. The voltage Vr flowing in the drain terminal of the transistor M0 is effected by the reference current I0 flowing in the reference resistance R0. The current mirror circuit 21 supplies the output currents I1, I2 that are equal to the reference current I0 to the detection elements H1, H2. Accordingly, the reference current I0 and the output currents I1, I2 may be inhibited from varying in response to mixed noises.

Figure 3:
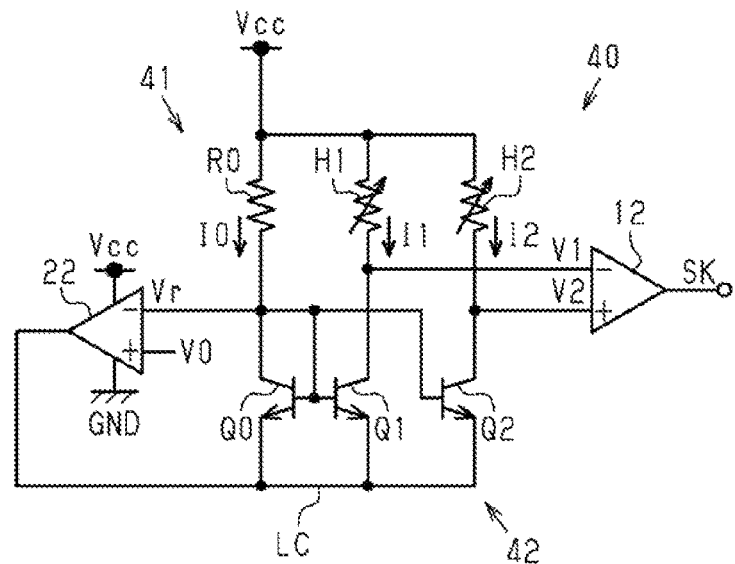
FIG. 3 is a schematic circuit diagram of a detection circuit of another example of the first embodiment.

Another example of the first embodiment will hereunder be explained. As shown in FIG. 3, a current source circuit 41 of a detection circuit 40 includes a current mirror circuit 42. The current mirror circuit 42 includes plural (three) transistors Q0, Q1, Q2 (i.e., serving as the first transistor and the second transistor). Each of the transistors Q0, Q1, Q2 corresponds to a negative-positive-negative bipolar transistor, or a NPN bipolar transistor. A collector terminal of the transistor Q0 is connected to the reference resistance R0. The collector terminals of the transistors Q1, Q2 are connected to the detection elements H1, H2, respectively. The collector terminal of the transistor Q0 is connected to the respective base terminals of the transistors Q0, Q1, Q2. Respective emitter terminals of the transistors Q0, Q1, Q2 are connected to the output terminal of the operational amplifier 22.

As such, similarly to the first embodiment, the detection circuit 40 including the current mirror circuit 42 that corresponds to the bipolar transistor may inhibit the output currents I1, I2 from varying due to the change of the temperature level. In addition, the output currents I1, I2 are inhibited from varying due to the mixture of noises.

A second embodiment will hereunder be explained. For convenience of description, the same components as those described in the first embodiment are marked with the same reference numerals, and a part of, or the all of the description of the components will not be repeated.

Figure 4:
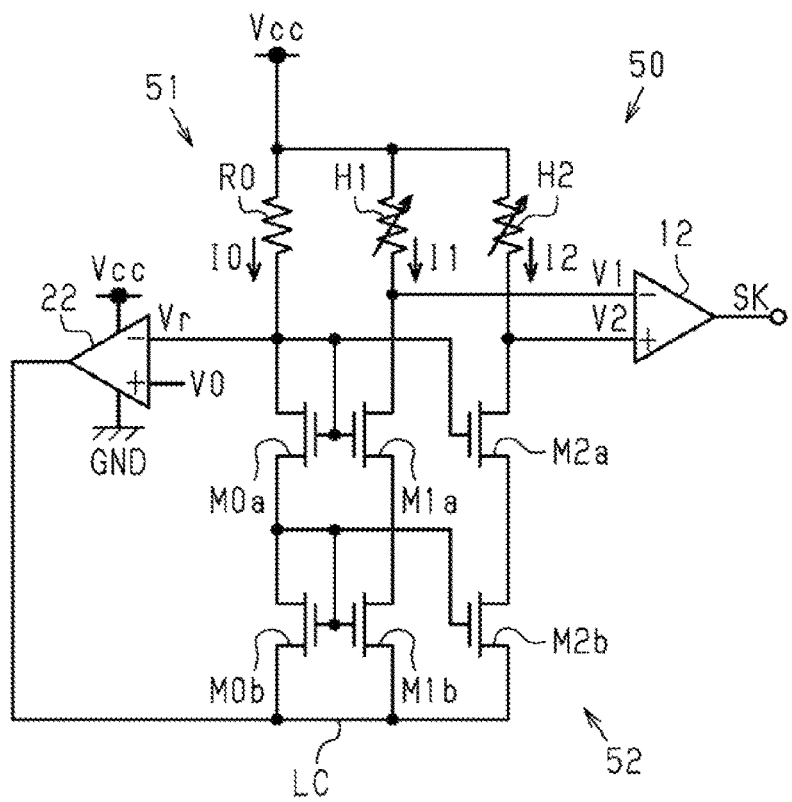
FIG. 4 is a schematic circuit diagram of a detection circuit according to a second embodiment.

As shown in FIG. 4, a detection circuit 50 includes a current source circuit (a constant current circuit) 51 and the differential amplifier 12. The current source circuit 51 supplies the output currents I1, I2 to the detection elements H1, H2.

The current source circuit 51 includes the reference resistance R0, a current mirror circuit 52, and the operational amplifier 22. The current mirror circuit 52 corresponds to a cascode current mirror circuit. Specifically, the current mirror circuit 52 includes two transistors M0a, M0b (i.e., serving as the first transistor) that are serially connected to the reference resistance R0. Similarly, the current mirror circuit 52 includes transistors M1a, M1b (i.e., serving as the second transistor) that are serially connected to the detection element H1, and transistors M2a, M2b (i.e., serving as the second transistor) that are serially connected to the detection element H2.

Each of the transistors M0a, M0b, M1a, M1b, M2a, M2b corresponds to the n-channel MOS transistor. Each of the transistors M0a, M1a, M2a has the same electrical characteristics with one another. Each of the transistors M0b, M1b, M2b has the same electrical characteristics with one another.

A second terminal of the reference resistance R0 is connected to the drain terminal of the transistor M0a. A source terminal of the transistor M0a is connected to a drain terminal of the transistor M0b. A source terminal of the transistor M0b is connected to the common wire LC. Similarly, the second terminal provided at the detection element H1 is connected to a drain terminal of the transistor M1a, and a source terminal of the transistor M1a is connected to a drain terminal of the transistor M1b. A source terminal of the transistor M1b is connected to the common wire LC. The second terminal provided at the detection element H2 is connected to a drain terminal of the transistor M2a. A source terminal of the transistor M2a is connected to a drain terminal of the transistor M2b. A source terminal of the transistor M2b is connected to the common wire LC.

A gate terminal of the transistor M0a is connected to the drain terminal of the transistor M0a and to the respective gate terminals of the transistors M1a, M2a. Similarly, the gate terminal of the transistor M0b is connected to the drain terminal of the transistor M0b and to respective gate terminals of the transistors M1b, M2b. That is, the current mirror circuit 52 corresponds to a cascode current mirror circuit.

As described above, according to the second embodiment, following effects and advantages may be attained.

The same effects and advantages as the first embodiment will be attained.

The current mirror 52 corresponds to a cascode current mirror circuit. Accordingly, in a case where the respective resistance values of the detection elements H1, H2 greatly vary, the output currents I1, I2 may be inhibited from varying. That is, the high-precision output currents I1, I2 may be supplied to the detection elements H1, H2, respectively.

Figure 5:
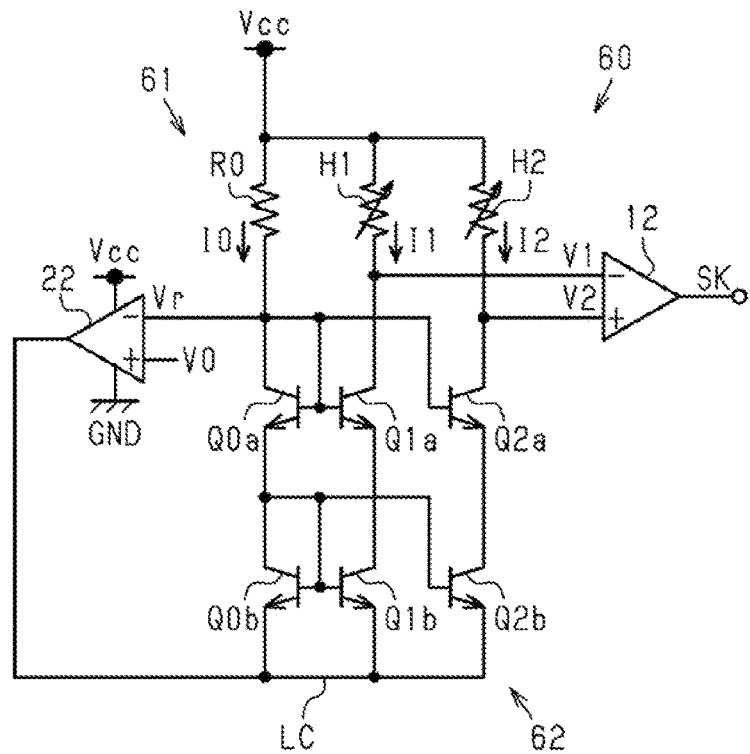
FIG. 5 is a schematic circuit diagram of a detection circuit of another example of the second embodiment.

Another example of the second embodiment will hereunder be explained. As shown in FIG. 5, a current source circuit 61 of a detection circuit 60 includes a current mirror circuit 62. The current mirror circuit 62 corresponds to a cascode current mirror circuit. Specifically, the current mirror circuit 62 includes two transistors Q0a, Q0b (i.e., serving as the first transistor) that are serially connected to the reference resistance R0. Similarly, the current mirror circuit 62 includes transistors Q1a, Q1b (i.e., serving as the second transistor) that are serially connected to the detection element H1, and transistors Q2a, Q2b (i.e., serving as the second transistor) that are serially connected to the detection element H2.

Each of the transistors Q0a, Q0b, Q1a, Q1b, Q2a, Q2b corresponds to, for example, the NPN bipolar transistor. The second terminal of the reference resistance R0 is connected to the collector terminal of the transistor Q0a. An emitter terminal of the transistor Q0a is connected to a collector terminal of the transistor Q0b. An emitter terminal of the transistor Q0b is connected to the common wire LC. Similarly, the second terminal provided at the detection element H1 is connected to a collector terminal of the transistor Q1a, and an emitter terminal of the transistor Q1a is connected to a collector terminal of the transistor Q1b. An emitter terminal of the transistor Q1b is connected to the common wire LC. The second terminal provided at the detection element H2 is connected to a collector terminal of the transistor Q2a. An emitter terminal of the transistor Q2a is connected to a collector terminal of the transistor Q2b. The emitter terminal of the transistor Q2b is connected to the common wire LC.

A base terminal of the transistor Q0a is connected to the collector terminal of the transistor Q0a, and to respective base terminals of the transistors Q1a, Q2a. Similarly, a base terminal of the transistor Q0b is connected to the collector terminal of the transistor Q0b, and to respective base terminals of the transistors Q1b, Q2b.

As such, similarly to the second embodiment, the detection circuit 60 including a cascode current mirror circuit that corresponds to the bipolar transistor may supply the high-precision output currents I1, I2 to the detection elements H1, H2, respectively. The output currents I1, I2 may be inhibited from varying due to the change of the temperature level. Moreover, the output currents I1, I2 may be inhibited from varying due to the mixture of noises.

A third embodiment will hereunder be explained. For convenience of description, the same components as those described in the first embodiment are marked with the same reference numerals, and a part of, or the all of the description of the components will not be repeated.

Figure 6:
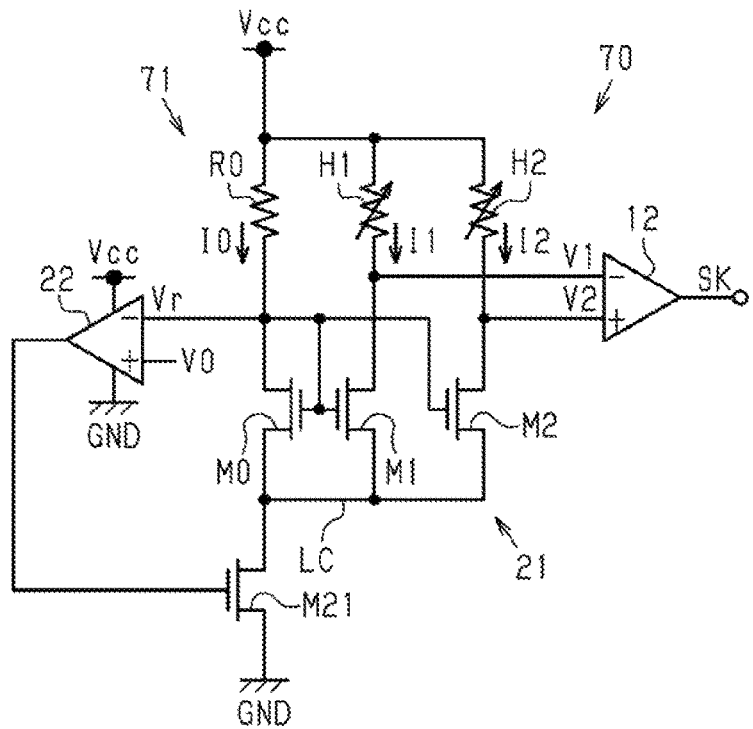
FIG. 6 is a schematic circuit diagram of a detection circuit according to a third embodiment.

As shown in FIG. 6, a detection circuit 70 includes a current source circuit (a constant current circuit) 71 and the differential amplifier 12. The current source circuit 71 includes the reference resistance R0, the current mirror circuit 21, the operational amplifier 22, and a transistor M21 (i.e., serving as a third transistor).

The transistor M21 corresponds to, for example, the n-channel MOS transistor. A drain terminal (a first terminal) of the transistor M21 is connected to the common wire LC. A source terminal (a second terminal) of the transistor M21 is connected to the power source wire GND. A gate terminal (a third control terminal) of the transistor M21 is connected to the output terminal of the operational amplifier 22. Accordingly, the operational amplifier 22 controls the voltage of the common wire LC via the transistor M21.

The current flowing in the transistors M0, M1, M2 of the current mirror circuit 21 flows to the power source wire GND via the transistor M21. Accordingly, the amount of the current of the reference current I0 and the amounts of the output currents I1, I2 at the current mirror circuit 21 may be increased equal to or greater than the supplying capacity of the operational amplifier 22. The low-resistance detection elements H1, H2 may be used.

According to the third embodiment, following effects and advantages may be attained.

The same effects and advantages as the first embodiment will be attained.

The respective currents flowing in the transistors M0, M1, M2 of the current mirror circuit 21 flows to the power supply wire GND via the transistor M21. Accordingly, the amount of the current of the reference current I0 and the respective amounts of the output currents I1, I2 at the current mirror 21 may be increased equal to or greater than the supplying capacity of the operational amplifier 22. That is, the detection element H1, H2 that easily flow the current may be used.

Another example of the third embodiment will hereunder be explained.

Figure 7:
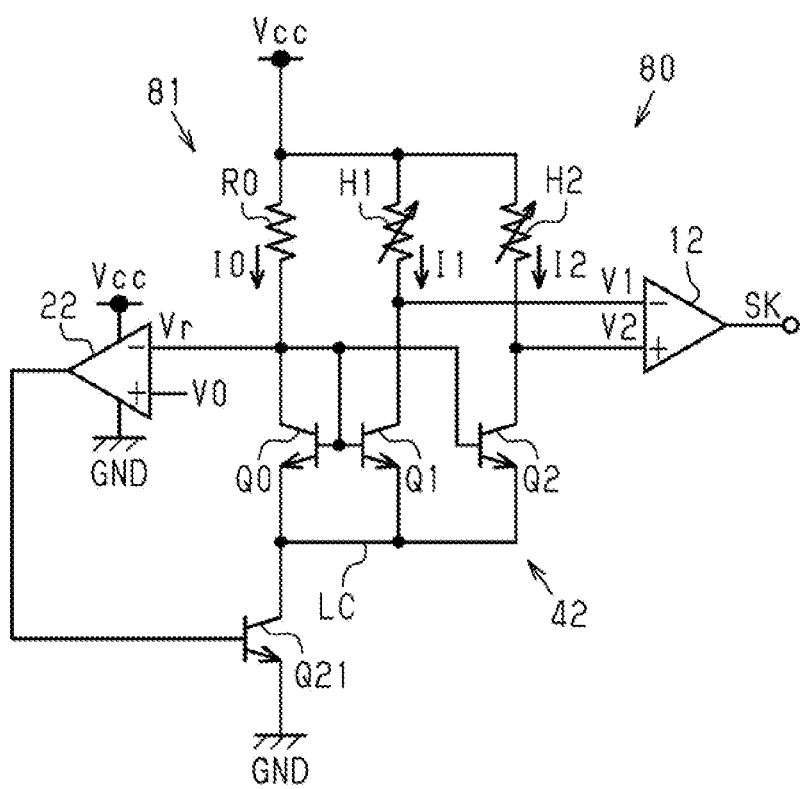
FIG. 7 is a schematic circuit diagram of the detection circuit of another example of the third embodiment.

As shown in FIG. 7, a current source circuit 80 of a detection circuit 80 includes the reference resistance R0, the current mirror circuit 42, the operational amplifier 22, and a transistor Q21 (i.e., serving as the third transistor). The transistor Q21 corresponds to, for example, the NPN bipolar transistor. A collector terminal (a first terminal) of the transistor Q21 is connected to the common wire LC. An emitter terminal (a second terminal) of the transistor Q21 is connected to the power source wire GND. A base terminal (the third control terminal) of the transistor Q21 is connected to the output terminal of the operational amplifier 22.

As such, similarly to the third embodiment, the amount of the current flowing in the reference resistance R0 and the respective amounts of the current flowing in the detection elements H1, H2 may be increased equal to or greater than the current supplying capacity of the operational amplifier 22 at the detection circuit 80 including the transistor Q21 that corresponds to a bipolar transistor. The low-resistance detection elements H1, H2 may be used.

The first, second and third embodiments may be conducted in the following manners.

A detection circuit may include one element, or three or more detection elements. For example, in a case where the detection circuit corresponds to one detection element (for example, the detection element H1 shown in FIG. 1), the detection signal SK is outputted in response to the voltage of the second terminal provided at the detection element, or is outputted by being amplified by the differential amplifier 12 to which the voltage corresponding to the reference voltage of the differential amplification is supplied.

According to the third embodiment and another example of the third embodiment, each of the current mirror circuits 21, 42 may correspond to a cascode current mirror circuit. The stage of the transistor of the cascode current mirror circuit may be three or more.

According to the first, second and third embodiments, each of the detection elements H1, H2 corresponds to a semiconductor strain gauge. Alternatively, for example, a wire strain gauge, a strain gauge having a pressure membrane resistance, or a foil strain gauge is applicable. Each of the detection elements H1, H2 may correspond to an element detecting the physical quantity of, for example, a magneto-resistance effect element, or a MR element, and a Hall element.

A p-channel MOS transistor or a PNP bipolar transistor may be used. In a case where the P-channel MOS transistor or the PNP bipolar transistor are used, the reference resistance R0 and the detection elements H1, H2 are connected to a wire to which a low-voltage power supply voltage GND is supplied.

According to the aforementioned embodiment, the current source circuit (11, 41, 51, 61, 71, 81) flowing an output current (I1, I2) to at least one detection element (H1, H2) including the first terminal to which the first voltage (Vcc) is supplied and the second terminal being connected to the current source circuit (11, 41, 51, 61, 71, 81) includes the reference resistance (R0) including the first terminal being connected to the first wire (Vcc) to which the first voltage (Vcc) is supplied, the current mirror circuit (21, 42, 52, 62) including at least one first transistor (M0, M0a, M0b, Q0, Q0a, Q0b) including the first terminal and the first control terminal that are connected to the second terminal of the reference resistance (R0), and at least one second transistor (M1, M1a, M1b, M2, M2a, M2b, Q1, Q1a, Q1b, Q2, Q2a, Q2b) including the second control terminal that is connected to the first control terminal (M0, M0a, M0b, Q0, Q0a, Q0b), the current mirror circuit (21, 42, 52, 62) in which the second transistor (M1, M1a, M1b, M2, M2a, M2b, Q1, Q1a, Q1b, Q2, Q2a, Q2b) includes the first terminal that is connected to the second terminal provided at the detection element (H1, H2), and in which the first transistor (M0, M0a, M0b, Q0, Q0a, Q0b) includes a second terminal that is connected to the second terminal provided at the second transistor (M1, M1a, M1b, M2, M2a, M2b, Q1, Q1a, Q1b, Q2, Q2a, Q2b), and the control circuit (22) controlling the voltage of the common wire (LC) that is connected to the second terminal provided at the first transistor (M0, M0a, M0b, Q0, Q0a, Q0b) and the second terminal provided at the second transistor (M1, M1a, M1b, M2, M2a, M2b, Q1, Q1a, Q1b, Q2, Q2a, Q2b) such that the voltage of the second terminal provided at the reference resistance (R0) comes to be equal to the reference voltage (V0, V0d, V0r).

According to the construction, for example, in a case where the temperature level changes, the voltage of the common wire LC is controlled in response to the characteristics of the first transistor (M0, M0a, M0b, Q0, Q0a, Q0b) in the temperature and the resistance value of the reference resistance R0 in the temperature. Accordingly, the terminal voltage of the reference resistance R0 comes to be equal to the reference voltage (V0, V0d, V0r). Thus, the temperature characteristics of the first transistor (M0, M0a, M0b, Q0, Q0a, Q0b) in response to the temperature change are inhibited from being affected relative to the current value of the reference current I0 flowing in the reference resistance (R0).

According to the aforementioned embodiment, the first transistor (M0, M0a, M0b, Q0, Q0a, Q0b) corresponds to the plural first transistors (M0a, M0b, Q0a, Q0b), the second transistor (M1a, M1b, M2a, M2b, Q1a, Q1b, Q2a, Q2b) corresponds to the plural second transistor (M1a, M1b, M2a, M2b, Q1a, Q1b, Q2a, Q2b), and the current mirror circuit (52, 62) corresponds to the cascode current mirror circuit in which the plurality of first transistors (M0a, M0b, Q0a, Q0b) is serially connected to one another and in which the plurality of second transistors (M1a, M1b, M2a, M2b, Q1a, Q1b, Q2a, Q2b) is serially connected to one another.

According to the aforementioned construction, the output current is inhibited from changing relative to the change of the resistance value of the detection element (H1, H2).

According to the aforementioned embodiment, the current source circuit (71, 81) further includes the third transistor (M21, Q21) including the first terminal that is connected to the common wire (LC), the third transistor (M21, Q21) including the second terminal that is connected to the second wire (GND) to which the second voltage (GND) that is different from the first voltage Vcc is supplied, the third transistor (M21, Q21) including the third control terminal that is connected to an output terminal of the control circuit (22). The control circuit (22) controls the voltage of the common wire (LC) via the third transistor (M21, Q21).

According to the aforementioned construction, the current flowing in the current mirror circuit (21, 42) flows in the second wire (GND) via the third transistor (M21, Q21). Accordingly, the amount of the current flowing in the current mirror circuit (21, 42) may be greater than the current supplying capability of the control circuit (22).

According to the aforementioned embodiment, the second transistors (M1, M1a, M1b, M2, M2a, M2b, Q1, Q1a, Q1b, Q2, Q2a, Q2b) corresponds to the plural second transistors (M1, M1a, M1b, M2, M2a, M2b, Q1, Q1a, Q1b, Q2, Q2a, Q2b). The detection element (H1, H2) corresponds to the plurality of detection elements (H1, H2). The plural second transistors (M1, M1a, M1b, M2, M2a, M2b, Q1, Q1a, Q1b, Q2, Q2a, Q2b) each flows the output current (I1, I2) to each of the plural detection elements (H1, H2).

According to the aforementioned construction, the output current that is equal to the reference current I0 is supplied to each of the plural detection elements (H1, H2).

According to the aforementioned embodiment, the detection element (H1, H2) corresponds to the strain gauge. The reference resistance (R0) is made from the same material as the material of the detection element (H1, H2).

According to the aforementioned construction, the temperature characteristics of the resistance values of the reference resistance R0 and the detection element (H1, H2) may be equal to each other. Accordingly, the voltage change of the output voltage of the strain gauge due to the temperature characteristics of the resistance value of the strain gauge when the strain gauge is not strained may be inhibited.

According to the aforementioned embodiment, the current source circuit (11, 41, 51, 61, 71, 81) further includes the voltage generation circuit (30) generating the reference voltage (V0, V0d), the voltage generation circuit (30) generating the reference voltage (V0, V0d) such that the reference voltage (V0, V0d) has the constant differential voltage relative to the first voltage Vcc.

According to the aforementioned construction, the voltage between the terminals of the detection element comes to be constant relative to the change of the first voltage Vcc. Accordingly, the response, or the sensitivity of the detection element (H1, H2) resulted from the change of the first voltage Vcc may be inhibited from changing.

According to the aforementioned embodiment, the current source circuit (11, 41, 51, 61, 71, 81) further includes the voltage generation circuit (30) generating the reference voltage (V0, V0r), the voltage generation circuit (30) generating the reference voltage (V0, V0r) that is in proportion to the first voltage Vcc.

According to the aforementioned construction, the response of the detection element (H1, H2) that is in proportion to the change of the first voltage Vcc may be specified. In a case where the reference voltage (V0, V0r) of a signal processing circuit to which the output of the detection element is inputted is in proportion to the first voltage Vcc, an error, or an inaccuracy when the signal processing circuit is inputted is inhibited.

According to the aforementioned embodiment, the detection circuit (10, 40, 50, 60, 70, 80) includes the two detection elements (H1, H2) corresponding to the first detection element (H1, H2) and the second detection element (H1, H2), the two detection elements (H1, H2) each including a first terminal to which a first voltage (Vcc) is supplied, the two detection elements (H1, H2) each changing a resistance value in response to a physical quantity of a detection target, the current source circuit (11, 41, 51, 61, 71, 81) being connected to the second terminals provided at the two detection elements (H1, H2), the current source circuit (11, 41, 51, 61, 71, 81) supplying the output current (I1, I2) to each of the detection elements (H1, H2), and the differential amplifier (12) including the input terminal being connected to the second terminals provided at the two detection elements (H1, H2), the differential amplifier (12) outputting detection signals by differently amplifying the input voltage (V1, V2). The first detection element (H1, H2) is disposed so as to change the resistance value of the first detection element (H1, H2) in response to the physical quantity of the detection target. The second detection element (H1, H2) is disposed such that the changing ratio of the resistance value of the second detection element (H1, H2) in response to the physical quantity of the detection target is different from the changing ratio of the resistance value of the first detection element (H1, H2). The current source circuit (11, 41, 51, 61, 71, 81) includes the reference resistance (R0) including the first terminal being connected to the first wire (Vcc) to which the first voltage (Vcc) is supplied, the current mirror circuit (21, 42, 52, 62) including the first transistor (M0, M0a, M0b, Q0, Q0a, Q0b) including the first terminal and the first control terminal that are connected to the second terminal provided at the reference resistance (R0), the two second transistors (M1, M1a, M1b, M2, M2a, M2b, Q1, Q1a, Q1b, Q2, Q2a, Q2b) each including the second control terminal that is connected to the first control terminal (M0, M0a, M0b, Q0, Q0a, Q0b), the current mirror circuit (21, 42, 52, 62) in which the two second transistors (M1, M1a, M1b, M2, M2a, M2b, Q1, Q1a, Q1b, Q2, Q2a, Q2b) includes the respective first terminals, each of the first terminals being connected to the second terminal provided at the detection element (H1, H2), and in which the first transistor (M0, M0a, M0b, Q0, Q0a, Q0b) includes the second terminal that is connected to each of the second terminals provided at the two second transistors (M1, M1a, M1b, M2, M2a, M2b, Q1, Q1a, Q1b, Q2, Q2a, Q2b), and the control circuit (22) including the first input terminal that is connected to the second terminal provided at the reference resistance (R0), the control circuit (22) including the second input terminal to which the reference voltage is supplied, the control circuit (22) controlling the voltage of the common wire (LC) that is connected to the second terminal provided at the first transistor (M0, M0a, M0b, Q0, Q0a, Q0b) and the respective second terminals provided at the two second transistors (M1, M1a, M1b, M2, M2a, M2b, Q1, Q1a, Q1b, Q2, Q2a, Q2b) such that the voltage of the second terminal provided at the reference resistance (R0) comes to be equal to the reference voltage (V0, V0d, V0r).

According to the construction, for example, in a case where the temperature level changes, the voltage of the common wire LC is controlled in response to the characteristics of the first transistor (M0, M0a, M0b, Q0, Q0a, Q0b) in the temperature and the resistance value of the reference resistance R0 in the temperature. Accordingly, the terminal voltage of the reference resistance R0 comes to be equal to the reference voltage (V0, V0d, V0r). Thus, the characteristic changes of the first transistor (M0, M0a, M0b, Q0, Q0a, Q0b) in response to the temperature change are inhibited from being affected relative to the current value of the reference current I0 flowing in the reference resistance (R0). Accordingly, the output current supplying to the detection element (H1, H2) is inhibited from changing. Moreover, because the detection circuit (10, 40, 50, 60, 70, 80) is differently constructed, the detection circuit (10, 40, 50, 60, 70, 80) may be inhibited from being affected by an in-phase noise. The impact to the change of offset due to the temperature level may be reduced.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. A current source circuit flowing an output current to at least one detection element including a first terminal to which a first voltage is supplied and a second terminal being connected to the current source circuit, comprising:
a reference resistance including a first terminal being connected to a first wire to which the first voltage is supplied;
a current mirror circuit including
at least one first transistor including a first terminal and a first control terminal that are connected to a second terminal of the reference resistance; and
at least one second transistor including a second control terminal that is connected to the first control terminal,
the current mirror circuit in which the second transistor includes the first terminal that is connected to the second terminal provided at the detection element, and in which the first transistor includes a second terminal that is connected to a second terminal provided at the second transistor; and
a control circuit controlling a voltage of a common wire that is connected to the second terminal provided at the first transistor and the second terminal provided at the second transistor such that a voltage of the second terminal provided at the reference resistance comes to be equal to a reference voltage.

2. The current source circuit according to claim 1, wherein
the first transistor corresponds to a plurality of first transistors,
the second transistor corresponds to a plurality of second transistor, and
the current mirror circuit corresponds to a cascode current mirror circuit in which the plurality of first transistors is serially connected to one another and in which the plurality of second transistors is serially connected to one another.

3. The current source circuit according to claim 1, further comprising:
a third transistor including a first terminal that is connected to the common wire, the third transistor including a second terminal that is connected to a second wire to which a second voltage that is different from the first voltage is supplied, the third transistor including a third control terminal that is connected to an output terminal of the control circuit, wherein
the control circuit controls the voltage of the common wire via the third transistor.

4. The current source circuit according to claim 2, further comprising:
a third transistor including a first terminal that is connected to the common wire, the third transistor including a second terminal that is connected to a second wire to which a second voltage that is different from the first voltage is supplied, the third transistor including a third control terminal that is connected to an output terminal of the control circuit, wherein
the control circuit controls the voltage of the common wire via the third transistor.

5. The current source circuit according to claim 1, wherein
the second transistors corresponds to a plurality of second transistors,
the detection element corresponds to a plurality of detection elements, and
the plurality of second transistors each flows the output current to each of the plurality of detection elements.

6. The current source circuit according to claim 2, wherein
the second transistors corresponds to a plurality of second transistors,
the detection element corresponds to a plurality of detection elements, and
the plurality of second transistors each flows the output current to each of the plurality of detection elements.

7. The current source circuit according to claim 3, wherein
the second transistors corresponds to a plurality of second transistors,
the detection element corresponds to a plurality of detection elements, and
the plurality of second transistors each flows the output current to each of the plurality of detection elements.

8. The current source circuit according to claim 1, wherein
the detection element corresponds to a strain gauge; and the reference resistance is made from a same material as a material of the detection element.

9. The current source circuit according to claim 2, wherein
the detection element corresponds to a strain gauge; and
the reference resistance is made from a same material as a material of the detection element.

10. The current source circuit according to claim 3, wherein
the detection element corresponds to a strain gauge; and
the reference resistance is made from a same material as a material of the detection element.

11. The current source circuit according to claim 5, wherein
the detection element corresponds to a strain gauge; and
the reference resistance is made from a same material as a material of the detection element.

12. The current source circuit according to claim 1, further comprising:
a voltage generation circuit generating the reference voltage, the voltage generation circuit generating the reference voltage such that the reference voltage has a constant differential voltage relative to the first voltage.

13. The current source circuit according to claim 1, further comprising:
a voltage generation circuit generating the reference voltage, the voltage generation circuit generating the reference voltage that is in proportion to the first voltage.

14. A detection circuit, comprising:
two detection elements corresponding to a first detection element and a second detection element, the two detection elements each including a first terminal to which a first voltage is supplied, the two detection elements each changing a resistance value in response to a physical quantity of a detection target;
a current source circuit being connected to second terminals provided at the two detection elements, the current source circuit supplying an output current to each of the detection elements; and
a differential amplifier including an input terminal being connected to the second terminals provided at the two detection elements, the differential amplifier outputting detection signals by differently amplifying an input voltage; wherein
the first detection element is disposed so as to change a resistance value of the first detection element in response to the physical quantity of the detection target;
the second detection element is disposed such that a changing ratio of a resistance value of the second detection element in response to the physical quantity of the detection target is different from a changing ratio of a resistance value of the first detection element; and
the current source circuit includes;
a reference resistance including a first terminal being connected to a first wire to which a first voltage is supplied;
a current mirror circuit including
a first transistor including a first terminal and a first control terminal that are connected to a second terminal provided at the reference resistance; and
two second transistors each including a second control terminal that is connected to the first control terminal,
the current mirror circuit in which the two second transistors includes respective first terminals, each of the first terminals being connected to a second terminal provided at the detection element, and in which the first transistor includes the second terminal that is connected to each of the second terminals provided at the two second transistors; and
a control circuit including a first input terminal that is connected to a second terminal provided at the reference resistance, the control circuit including a second input terminal to which the reference voltage is supplied, the control circuit controlling a voltage of a common wire that is connected to the second terminal provided at the first transistor and the respective second terminals provided at the two second transistors such that a voltage of the second terminal provided at the reference resistance comes to be equal to a reference voltage.

* * * * *